US011259547B2

United States Patent
Bruggeman et al.

(10) Patent No.: US 11,259,547 B2
(45) Date of Patent: Mar. 1, 2022

(54) COMPOSITION AND FEED CONTAINING MEDIUM-CHAIN FATTY ACIDS

(71) Applicant: NUTRITION SCIENCES N.V., Drongen (BE)

(72) Inventors: Geert Bruggeman, Bruges (BE); Katrien Deschepper, De Pinte (BE)

(73) Assignee: Nutrition Sciences N.V., Drongen (BE)

( * ) Notice: Subject to any disclaimer, the term of this patent is extended or adjusted under 35 U.S.C. 154(b) by 0 days.

(21) Appl. No.: 15/023,512

(22) PCT Filed: Oct. 9, 2014

(86) PCT No.: PCT/IB2014/065172
§ 371 (c)(1),
(2) Date: Mar. 21, 2016

(87) PCT Pub. No.: WO2015/052673
PCT Pub. Date: Apr. 16, 2015

(65) Prior Publication Data
US 2016/0205970 A1 Jul. 21, 2016

(30) Foreign Application Priority Data

Oct. 9, 2013 (BE) .................... 2013/0677

(51) Int. Cl.
*A61K 31/20* (2006.01)
*A61P 31/04* (2006.01)
*A23K 20/158* (2016.01)
*A23K 50/10* (2016.01)
*A23K 50/60* (2016.01)
*A61K 9/00* (2006.01)
*A61K 45/06* (2006.01)

(52) U.S. Cl.
CPC ............ *A23K 20/158* (2016.05); *A23K 50/10* (2016.05); *A23K 50/60* (2016.05); *A61K 9/0056* (2013.01); *A61K 31/20* (2013.01); *A61K 45/06* (2013.01)

(58) Field of Classification Search
CPC ........ A23K 20/158; A61P 31/04; A61K 31/20
See application file for complete search history.

(56) References Cited

U.S. PATENT DOCUMENTS

| 5,208,257 | A | | 5/1993 | Kabara | |
| 5,462,967 | A | * | 10/1995 | Hayashi | A61K 31/23 426/2 |
| 6,635,303 | B1 | | 10/2003 | Youcheff et al. | |
| 6,638,978 | B1 | * | 10/2003 | Kabara | A01N 37/02 514/550 |
| 7,261,888 | B1 | * | 8/2007 | Decuypere | A23K 20/158 424/94.6 |
| 9,271,517 | B2 | | 3/2016 | Bruggeman et al. | |
| 2005/0100584 | A1 | * | 5/2005 | Miller | A61K 31/225 424/442 |
| 2007/0219270 | A1 | * | 9/2007 | Bruggeman | A23K 1/164 514/558 |
| 2009/0275657 | A1 | | 11/2009 | Dee et al. | |

FOREIGN PATENT DOCUMENTS

| EP | 1106077 A1 | 6/2001 |
| JP | 08-175989 A | 7/1996 |
| WO | WO 2006/002927 A2 | 1/2006 |
| WO | WO 2008/061078 A2 | 5/2008 |
| WO | WO 2013/184879 A2 | 12/2013 |

OTHER PUBLICATIONS

Van Meenen, E. Oral supplementation of medium chain fatty acids for better immunity. Int. Dairy Topics 10(1), p. 11 (2011).*
Piepers et al. Oral supplementation of medium-chain fatty acids during the dry period supports the neutrophil viability of peripartum dairy cows. J. Dairy Res. 80, pp. 309-318 (Apr. 2013).*
Hill et al. Fatty acid intake alters growth and immunity in milk-fed calves. J. Dairy Sci. 94, pp. 3936-3948 (2011).*
Van Meenen, E. Vitamex presentation: Effects of Medium Chain Fatty Acids on Rumen Fermentation. EAAP 2009, Barcelona (2009).*
Caro et al., "Enzymatic synthesis of medium-chain triacylglycerols by alcoholysis and interesterification of copra oil using a crude papain lipase preparation," *European Journal of Lipid Science Technology*, vol. 106(8), pp. 503-512 (2004).
Nair et al., "Antibacterial Effect of Caprylic Acid and Monocaprylin on Major Bacterial Mastitis Pathogens," *Journal of Dairy Science*, American Dairy Science Association, vol. 88(10), pp. 3488-3495 (Oct. 1, 2005).

* cited by examiner

*Primary Examiner* — Jeffrey S Lundgren
*Assistant Examiner* — Chris E Simmons
(74) *Attorney, Agent, or Firm* — Knobbe, Martens, Olson & Bear, LLP

(57) ABSTRACT

The present invention concerns a composition containing medium-chain fatty acids or salts or mono-, di-, triglycerides, esters or amide derivatives of medium-chain fatty acids. In a further aspect, the present invention concerns also a feed, supplemented with the composition, and a method for feeding animals, in particular calves, cattle and dairy cattle.

11 Claims, 1 Drawing Sheet

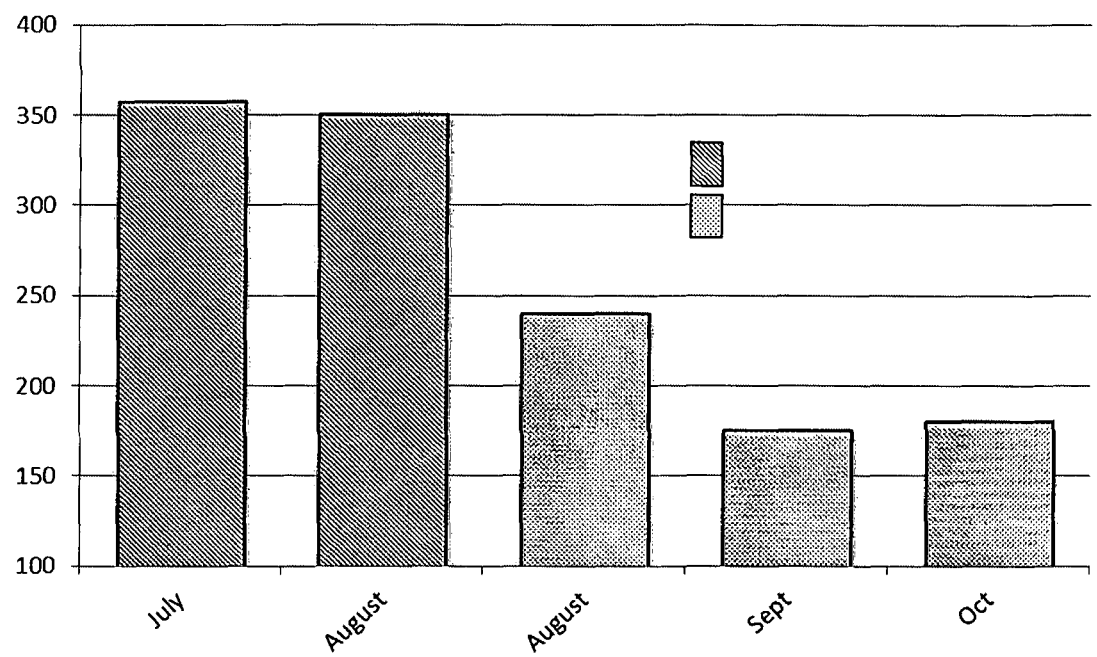

COMPOSITION AND FEED CONTAINING MEDIUM-CHAIN FATTY ACIDS

CROSS-REFERENCE TO RELATED APPLICATIONS

This application is the U.S. National Phase under 35 U.S.C. § 371 of International Application PCT/IB2014/065172, filed Oct. 9, 2014, which claims priority to BE 2013/0677, filed Oct. 9, 2013.

TECHNICAL FIELD

The present invention relates to a composition and animal feed comprising medium-chain fatty acids for the improvement of the immunity and intestinal health of animals, as well as for the elimination of harmful pathogens.

STATE OF THE ART

The optimization of animal feed efficiency, the damming of infections and the animal growth that is directly related to this, can have a significant influence on, among other things, the ecological footprint of the meat industry. High feed costs are reduced and maintenance costs of food-producing animals are decreased, which also leads to directly optimizing of the profits. The positive characteristics of medium-chain fatty acids as composition for animals have previously been known. EP 1 294 37 and EP 1 765 318 both describe a feed, supplemented with a composition consisting of medium-chain fatty acids having 6 to 10 carbon atoms. These additives have both a positive influence on the elimination or reduction of microbial pathogens in the feed (food congenital pathogens), as well as in the body (for example, gastro-intestinal tract) of animals.

Cattle and dairy cattle in particular, are, for example, highly susceptible to bacterial infections that lead to a mammary gland or udder inflammation. This phenomenon is generally known under the term mastitis. The inflammation is caused by various bacteria, such as *Streptococcus uberis, Streptococcus agalactiae, Prothoteca, E. coli, Staphylococcus aureus* and *Klebsiella*. The *E. coli* bacteria is the most common cause of mastitis. To date, the use of antibiotics is, for the time being, the most effective remedy at mastitis. In addition, the rule is: the earlier the treatment starts, the better it is. Bacteria can start to incorporate in the inflammatory tissue and thus become inaccessible to antibiotics. In occasional cases, mastitis is the result of a mold infestation.

Mastitis is now the most common health problem in dairy farms.

Medium-chain fatty acids serve as an alternative to the administration of antibiotics as a treatment for mastitis. Nair et al., 2005, describes the use of medium-chain fatty acids against mastitis. US 5 20 827 and US 2009 027 657 both describe the topical treatment of mastitis with a composition of medium-chain fatty acids or derivatives thereof. However, oral administration is not mentioned.

The mutual ratios between the medium-chain fatty acids which are present in the state of the art provide less than optimal ratios and are not well balanced. A good balancing of the composition of feed additives on the basis of different medium-chain fatty acids is, however, crucial. After all, a non-optimal concentration of the medium-chain fatty acids may have the result it is less or even not effective. Another problem with composition on the basis of medium-chain fatty acids is related to the strong, unpleasant smell of some of these medium-chain fatty acids or derivatives, as experienced by the animals. Thus, an animal will not be or be less inclined to eat a non-optimally balanced composition. It is the object of the present invention to provide a composition with an optimal composition of medium-chain fatty acids, ensuring that both the efficient intake of the medium-chain fatty acids as well as the ratios between the individual fatty acid chains are optimized, in order to thereby obtain an optimal effect. Furthermore, it is also object of the present invention to provide a composition of medium-chain fatty acids that is optimized for particular groups of animals, to thereby improve the general health of these animals and to prevent or to suppress any diseases. In particular, it is the intention to provide an alternative treatment for mastitis or udder inflammation in dairy cattle, the treatment providing an alternative to the conventional antibiotic use with dairy cows.

SUMMARY OF THE INVENTION

The present invention relates to a composition according to claim 1 and an animal feed according to claim 9. Preferably, the composition and feed are suitable for ruminant animals, such as cattle, dairy cattle and calves. Thus, the present invention aims to provide a balanced composition of medium-chain fatty acids that will have an improved effect on the general welfare of the animal, as well as the feed efficiency.

In a further aspect, the present invention relates to a method according to claim 12, in order to improve the health of an individual, to increase the weight gain, to increase the daily nutritional intake, to decrease the feed conversion and to generally increase the well-being by means of administrating the composition of the feed as herein described according to the invention.

DESCRIPTION OF THE FIGURES

FIG. 1 shows the evolution of the somatic cell count of dairy cows before the administration of a composition or animal feed according to an embodiment of the present invention and after administration of such a composition or feed.

DETAILED DESCRIPTION

The invention relates to a composition with an optimal ratio of medium-chain fatty acids, suitable for use in an animal feed. The composition will in particular therefore be administered orally. The animal feed, supplemented with the composition of the present invention, possesses an anti-microbial effect, and further also has a beneficial effect on the gastrointestinal tract and on the overall immunity of the animals fed with this feed. The feed additive and feed according to present invention also provides an improved feed conversion.

Unless defined otherwise, all terms used in the description of the invention, including technical and scientific terms, have the meaning as they are commonly understood by the skilled person in the technical field of the invention. The following terms are explicitly explained for a better assessment of the description of the invention.

"A", "an" and "the" refer in this document to both the singular and the plural, unless the context clearly implies otherwise. For example, "a segment" means one or more than one segment.

Where "approximately" or "about" is used in this document with a measurable quantity, a parameter, a time period or time, and the like, then variations are intended of +/−20% or less, preferably +/−10% or less, more preferably +/−5% or less, even more preferably +/−1% or less, and even more preferably +/−0.1% or less than the value cited, to the extent that such variations are applicable in the described invention. However, it should be understood that the value of the quantity with which the term "approximately" or "about" is used, is specifically disclosed in itself.

The terms "comprise", "comprising", "consist of", "consisting of", "provided", "include", "including", "contain", "containing", "hold", "holding" are synonyms and are inclusive or open terms that indicate the presence of what follows, and which do not exclude or prevent the presence of other components, characteristics, elements, members, steps, as known from or disclosed in the state of the art.

The citation of numeric interval by the endpoints includes all integer numbers, fractions, and/or real numbers between the endpoints, these endpoints included. In a first aspect, the invention relates to a composition comprising medium-chain fatty acids or $NH_4^+$-, $Na^+$-, $K^+$- and/or $Ca^{2+-}$ salts, mono-, di-, triglycerides, esters or amides thereof for use as a composition in animals. As described herein, the term "medium-chain fatty acids" or "MCFA" refers to fatty acids with a medium-chain length, wherein the fatty acids may be saturated or unsaturated. According to the invention, the MCFAs can consist of 6 to 12 carbon atoms, in particular, caproic acid (C6), caprylic acid (C8), capric acid (C10) or lauric acid (C12).

Preferentially, the feed comprises a mixture of medium-chain fatty acids, whereby these preferably have a chain length of 6 to 12 carbon atoms. In particular, the composition will comprise medium-chain fatty acids, selected from the group, consisting of caproic acid (C6), caprylic acid (C8), capric acid (C10) and lauric acid (C12).

In one embodiment, the medium-chain fatty acids are chemically modified, and the medium-chain fatty acids are provided with side-chains, such as, without limitation, one or more alkyl groups, preferably C1-C10 alkyl groups, in particular methyl or ethyl groups.

In a further embodiment, present invention comprises derivatives of medium-chain fatty acids. As described herein, the term "derivative of a medium-chain fatty acid" refers to a fatty acid chain of which the carboxyl group is reversibly converted to a different group, preferably, but without limitation, to an amide, salt, ester or glyceride. As described herein, the term "free fatty acids" refers to fatty acids that are not converted into a salt or a derivative (such as an amide, ester or glyceride). The use of esters and salts, for example, prevents the diffusion of bad odors, which may occur when the free fatty acids are used.

The ratios between the various medium-chain fatty acids from the present invention has been so determined to achieve optimal efficacy. The term "ratio" from the present invention should be understood as a ratio between the amounts of medium-chain fatty acids, and can be interpreted as either a weight or volume ratio.

The composition will preferably at least comprise caprylic acid (C8) and capric acid (C10), wherein the ratio of caprylic acid (C8) to capric acid (C10) is at least 0.6. In a further preferred embodiment, this ratio will be maximum 2.

A preferred embodiment of the composition according to present invention will, therefore, comprise C8 and C10 medium-chain fatty acids in a following ratio: $0.6<(C8/C10)<2$.

In a further embodiment, the composition according to the present invention, will comprise C8 and C10 medium-chain fatty acids, in a following ratio: $0.6<(C8/C10)<1.5$.

In a preferred embodiment, the composition will also include lauric acid (C12). Preferably, the ratio between the sum of caprylic acid and capric acid (C8+C10) and lauric acid (C12) in the composition will be at least 0.6. In a further preferred embodiment, this ratio will be maximum 1.5. A preferred embodiment of the composition according to the present invention will, therefore, comprise C8, C10 and C12 medium-chain fatty acids in a following ratio: $0.6<(C8+C10)/C12<1.5$.

In one embodiment, the composition or the feed according to the invention as described herein, is used for the selective elimination, suppression or regulation of one or more enteropathogens, selected from the group consisting of filamentous micro-organisms and micro-organisms with adhesion structures, Gram-negative bacteria, Gram-positive bacteria, fungi, yeast, and viruses. The term "(entero)pathogens," as opposed to "beneficial or non-pathogenic gastrointestinal microbial flora" means herein micro-organisms which have a detrimental effect to the host, and in particular which cause diseases or ailments. Other forms of adverse effects are reduced daily food intake, reduced daily weight gain, decreased feed conversion and reduced overall health and wellness.

In one embodiment, the composition or the feed according to the invention as described herein are administered to animals which are selected from the group consisting of fish, amphibians, reptiles, birds and mammals, such as, without limitation, adult or juvenile ruminant animals, sheep, goats, cattle, pigs, horses, poultry, fowl, domestic animals (e.g. dogs, cats, rabbits, hamsters, guinea pigs), and preferably selected from the group consisting of poultry, pigs and ruminants. More in particular, the composition or the feed is administered to ruminants such as cattle, dairy cattle and calves.

In particular, the composition according to the present invention, and the feed, supplemented with this composition, will provide an improved intestine and will increase the overall immunity in animals. In ruminants, this will also lead to a better rumen fermentation through a positive effect on the rumen flora.

In a further embodiment, the composition according to the present invention is intended for preventing and treating mastitis in dairy cattle. In particular, the composition according to the present invention will be suitable for inhibiting the growth and/or killing of bacteria involved in the pathogenesis of mastitis.

Following positive effects were generally observed:
Reduction of the cell count an prevention of clinical mastitis;
Reduced risk of acidosis by increased rumen pH;
More efficient use of nitrogen: reduced milk urea, reduced $NH_3$—concentration in the rumen;
Tendency for higher milk protein and less milk fat;
Improved feed efficiency;
Reduced methane emissions;
Lower veterinary costs through better resistance and general health;
Increasing the milk production in dairy cattle
Increasing the immunity in calves, cattle and dairy cattle;
Improving meat production in calves, cattle or dairy cattle; or
Improving rumen fermentation in cattle and dairy cattle.

As stated, the composition according to the present invention is effective, in particular for treatment of, or curing of, or suppressing of mastitis in dairy cattle and the associated signs and symptoms. Mastitis (breast inflammation, inflammation of the udder or milk gland inflammation) is an inflammation of the mammary gland which can be caused by a sterile inflammatory response of the body to the pressure of accumulating milk or by various kinds of pathogenic bacteria. Mastitis is a common disease in dairy cattle with a significant economic impact. It results in a reduction in milk production and in a change in the milk composition. Also, the number of somatic cells in the milk increases.

The amount of lactose and chlorine are positively correlated with each other. This is due to the activity of the udder, which keeps the milk isotonic. When the production of lactose is prevented due to an inflamed udder, it will issue more chlorides to the milk. This phenomenon can be used to detect mastitis. The number of Koestler (=100*chlorides/%lactose) is a reliable parameter to distinguish normal milk from mastitis milk. In normal milk, this number is 1.5-3.0; in mastitis milk, it is more than 3.

The somatic cell count of milk or cow cell count is also a criterion for the detection of mastitis. This number represents the number of cells per milliliter (ml) of milk, mostly white blood cells and epithelial cells. Generally, it can be said that 100,000 cells per ml is considered as the limit, an cell count above this 100,000 being an indication of mastitis.

Udder inflammation can be caused by bacteria of the strains *Staphylococous, Escherichia* and *Streptococcus*, such as there are *Staphylococcus aureus, Escherichia coli* and *Streptococcus uberis*. Conventional treatment is to treat the diseased cow with antibiotics and analgesics. In the light of a desired reduction in the use of antibiotics in cattle, it is thus necessary to provide an alternative treatment. In one embodiment of the present invention, the composition as well as the feed, are therefore suitable for the inhibition and elimination of *Staphylococcus, Escherichia*, and/or *Streptococcus*. In a further embodiment, the composition and the feed is appropriate for the inhibition and elimination of *Streptococcus agalactiae, Streptococcus dysgalactiae, Streptococcus uberis, Staphylococcus aureus* and/or *Escherichia coli*.

In one embodiment, the composition according to the invention, as described herein, comprises additional raw materials (additives) and/or growth-promoting substances. The additives are, in a preferred embodiment, selected from the group consisting of aroma's and plant extracts. In a further preferred embodiment, the growth-promoting components are selected from the group, consisting of antibiotics, vitamins, trace elements, probiotics, prebiotics, essential oils, enzymes, fatty acids, and (in)organic acids. Non-limiting examples of organic acids which can be used in an embodiment of the invention, comprise C1-C12 carboxylic acids, in particular unsubstituted carboxylic acids such as formic acid, acetic acid, propionic acid, butyric acid and valeric acid; and/or substituted carboxylic acids such as adipic acid, maleic acid, succinic acid, citric acid, fumaric acid, tartaric acid, lactic acid, gluconic acid, succinic acid and ascorbic acid, including cyclic carboxylic acids such as picolinic acid. The organic acids may contain one or more substituted or unsubstituted carboxylic acids, as well as mixtures thereof, as well as saturated, unsaturated, cyclic, and/or aliphatic carboxylic acids or mixtures thereof, as well as metal complexes and/or salts thereof, as well as racemic and/or enantiomeric forms thereof. Non-limiting examples of inorganic acids which can be used in an embodiment of the invention include strong acids in small amounts, such as perchloric acid (hyperchloric acid), hydrogen iodide, hydrogen bromide (hydrobromic acid), hydrogen chloride (hydrochloric acid), sulfuric acid and nitric acid; as well as weak inorganic acids such as phosphoric acid, hydrofluoric acid, hypochlorous acid, and nitrous acid.

In one embodiment, the medium-chain fatty acids in the composition according to the invention are present in liquid or solid form. In a further embodiment, the composition according to the invention as described herein, is formulated as a liquid or a solid form. The term "solid form" means a powder in particular. The term "liquid form", in particular, means a solution in water or means a solution in oil. The medium-chain fatty acids as described herein according to the invention are oil-soluble and can be provided both as powder and as an oil-solution. In particular, the composition is suitable for oral administration.

In one embodiment, the concentration of the medium-chain fatty acid, as described herein, amounts at least 1, 5, 10, 15, 20, 25, 30, 35, 40, 45, 50, 55, 60, 65, 70, 75, 80, 85, 90, 95, 99% by weight of the composition. In a further embodiment, the medium-chain fatty acids, as described herein, amounts to (based on dry weight) between 1 g/100 g composition (1% by weight) and 100 g/100 g composition (100% by weight), preferably between 50 g/100 g and 90 g/100 g composition (50-90% by weight), more preferably between 60 g/100 g and 80 g/100 g. This is to mean that the concentration of the MCFAs such as described herein maximally amounts to 100% by weight of the composition.

In a second aspect, the present invention includes an animal feed, supplemented with the composition according to the invention. Conventional animal feed naturally contains no or only a minimal amount of free medium-chain fatty acids. Addition of the composition of the present invention to the animal feed results in an animal feed which comprises medium-chain fatty acids (MCFA). In a preferred embodiment these MCFA will at least comprise caprylic acid (C8) and capric acid (C10) or a derivative thereof. In a further embodiment the ratio between the ratio between caprylic acid (C8) and capric acid (C10) will be at least 0.6 and maximum 2, in a further preferred embodiment maximum 1.5.

Preferably, the supplemented feed also includes lauric acid (C12) or a derivative, wherein the ratio between the sum of caprylic acid and capric acid (C8+C10) or derivatives and lauric acid (C12) or derivative in the composition amounts at least 0.6 and maximum 1.5.

In a further embodiment, the feed of the invention comprises up to 10% by weight of the medium-chain fatty acids (or salts, derivatives, or mixtures), as described herein. In particular the inclusion amount of the composition in the feed, will preferably be between 0.1 and 2 g/kg by dry weight of the feed. In a further embodiment, the feed comprises an amount of medium-chain fatty acids (or salts, derivatives, or mixtures), as described herein (based on dry weight) of between 0.01 g/100 g of dietary supplement (0.01% by weight) and 1 g/100 g of a dietary supplement, (1% by weight), preferably 0.07 g/100 g of food supplement (0.07% by weight).

Preferably the inclusion amount of the composition will ensure that an animal that is fed with the feed, obtains the composition in an amount between 0.1 and 2 g MCFA/kg dry matter in feed/day/animal.

In what follows, the invention is described by means of non-limiting examples which illustrate the invention, and which are not intended nor should be construed to limit the scope of the invention.

EXAMPLES

Example 1

45 dairy cows with an average milk production of 9,000 kg/year, but which suffer from subclinical mastitis were fed with a composition of MCFAs according to the following ratio:

C8/C10=1.0

(C8+C10)/C12=1.0

Another group was fed with a control composition without the medium-chain fatty acids.

Before the start of the experiment, these dairy cows already suffered from (clinical or visible) mastitis and they showed during 8 months before the therapy a consistently high somatic cell count of 350,000-400,000 cells/ml. Despite many efforts (milking machine control and hygiene) the increased cell count could not be reduced. As a therapy, the cows were then fed with a composition as described above, to an effective absorption amount of 0.5 g MCFA/kg dry feed/animal/day. The somatic cell count was recorded over the following months after the start of the experiment. The evolution of the cell count for both groups is given in FIG. 1.

From the data it is clear that the number in the group of cows that were fed with a composition according to the present invention decreased. This was not the case in the control group. Furthermore, apart from a reduction in somatic cell count, in addition no cases of clinical mastitis were observed.

In summary, it appears that composition of the present invention succeeded where management control failed: decreasing the cell count and reducing, treating or curing clinical mastitis. This also had a positive effect on the general health of the animal as well as the quality of milk.

It is believed that the present invention is not limited to the embodiments described above and that a number of modifications to the described examples can be added without having to re-evaluate the appended claims.

The invention claimed is:

1. A method for treating and preventing mastitis in an animal comprising administering a composition to an animal, wherein the composition consists essentially of fatty acids consisting of caprylic acid (C8), capric acid (C10) and lauric acid (C12), without caproic acid (C6), and wherein the ratio of caprylic acid (C8) to capric acid (C10) is at least 0.6 and maximum 1.5 and wherein the ratio between the sum of caprylic acid and capric acid (C8+C10) and lauric acid (C12) in the composition amounts to at least 0.6 and maximum 1.5.

2. The method according to claim 1, wherein the composition further comprises vitamins, trace elements, or minerals.

3. The method according to claim 1, wherein the composition is suitable for calves, cattle and dairy cattle.

4. The method according to claim 1, wherein the composition is administered orally.

5. Method according to 4, wherein the animal is fed on a daily basis.

6. The method according to claim 4, wherein the composition is included in an animal feed at between 0.1 and 2 g/kg of dry weight of the feed.

7. The method according to claim 6, wherein the animal is fed on a daily basis.

8. The method according to claim 4, wherein the composition is administered as a supplement to animal feed.

9. The method according to claim 8, wherein the animal is fed on a daily basis.

10. The method according to claim 8, wherein the inclusion amount of the composition ensures that an animal, fed with the animal feed, obtains the composition at a level of between 0.1 and 2 g MCFA/ kg dry matter in feed/day/animal.

11. The method according to claim 10, wherein the animal is fed on a daily basis.

* * * * *